(12) United States Patent
De Theije et al.

(10) Patent No.: US 9,778,254 B2
(45) Date of Patent: Oct. 3, 2017

(54) METHODS AND SYSTEMS FOR DETECTING

(75) Inventors: Femke Karina De Theije, Eindhoven (NL); Thea Van Der Wijk, Eindhoven (NL); Albert Hendrik Jan Immink, Eindhoven (NL); Eduard Gerard Marie Pelssers, Eindhoven (NL); Wilhelmina Maria Hardeman, Eindhoven (NL); Sandra Marlin, Didcot (GB); Gordon Thomas Jowett, Witney (GB)

(73) Assignees: KONINKLIJKE PHILIPS N.V., Eindhoven (NL); CONCATENO UK LIMITED, Abingdon, Oxfordshire (GB)

( * ) Notice: Subject to any disclaimer, the term of this patent is extended or adjusted under 35 U.S.C. 154(b) by 651 days.

(21) Appl. No.: 12/669,217

(22) PCT Filed: Jul. 18, 2008

(86) PCT No.: PCT/IB2008/052897
§ 371 (c)(1),
(2), (4) Date: Jun. 2, 2010

(87) PCT Pub. No.: WO2009/013683
PCT Pub. Date: Jan. 29, 2009

(65) Prior Publication Data
US 2010/0297780 A1    Nov. 25, 2010

(30) Foreign Application Priority Data
Jul. 20, 2007 (EP) ................................ 07112829

(51) Int. Cl.
*G01N 27/74* (2006.01)
*G01N 33/543* (2006.01)

(52) U.S. Cl.
CPC ..... *G01N 33/54366* (2013.01); *G01N 27/745* (2013.01); *Y10T 29/49885* (2015.01)

(58) Field of Classification Search
None
See application file for complete search history.

(56) References Cited

U.S. PATENT DOCUMENTS 5,110,727 A * 5/1992 Oberhardt ........................ 435/13
5,601,991 A * 2/1997 Oberhardt ..................... 435/7.91
(Continued)

FOREIGN PATENT DOCUMENTS

| JP | 2006-184250 A1 | 7/2006 |
| JP | 2007-139781 A1 | 6/2007 |
| WO | 2005116661 A1 | 12/2005 |

OTHER PUBLICATIONS

Fukumoto, H. et al "Rapid and High Sensitive Bio-Sensing System Utilizing Magnetic Beads" Solid_State Sensors, Actuators and Microsystems, 2005, The 13th International Conf. Jun. 5-9, 2005, pp. 1780-1783.

*Primary Examiner* — Rebecca Martinez
(74) *Attorney, Agent, or Firm* — Bacon & Thomas, PLLC

(57) ABSTRACT

A system and method wherein components of a reagent such as labeled antibodies are separated from a biologically active sensor surface by depositing the reagent on a carrier surface distinct from a sensor surface in a detection region. The present device provides a short, well-defined and controlled, pre-incubation time between the particles of interest in the sample fluid and the reagent, thereby increasing the reproducibility by providing all components in one detection region such as a detection chamber.

28 Claims, 7 Drawing Sheets

(56) References Cited

U.S. PATENT DOCUMENTS

| | | | |
|---|---|---|---|
| 5,922,537 A * | 7/1999 | Ewart et al. | 435/6.11 |
| 2001/0053535 A1* | 12/2001 | Bashir et al. | 435/34 |
| 2002/0119482 A1* | 8/2002 | Nelson et al. | 435/6 |
| 2003/0124623 A1* | 7/2003 | Yager et al. | 435/7.5 |
| 2004/0018611 A1* | 1/2004 | Ward et al. | 435/287.2 |
| 2005/0100930 A1 | 5/2005 | Wang | |
| 2006/0078472 A1* | 4/2006 | Momiyama | B01F 9/0016 422/400 |
| 2006/0134713 A1 | 6/2006 | Rylatt et al. | |
| 2009/0054255 A1* | 2/2009 | Lee et al. | 506/9 |
| 2010/0009456 A1* | 1/2010 | Prins et al. | 436/164 |
| 2010/0233824 A1* | 9/2010 | Verhoeckx et al. | 436/501 |

\* cited by examiner

METHODS AND SYSTEMS FOR DETECTING

FIELD OF THE INVENTION

The present invention relates to the field of biosensors. More particularly, the present invention relates to methods and systems for obtaining devices for detecting the presence of an analyte, e.g. for qualitative or quantitative detection of biological, chemical or biochemical entities.

BACKGROUND OF THE INVENTION

Biosensors are devices that allow qualitative or quantitative detection of target molecules, also called "analytes", such as e.g. proteins, viruses, bacteria, cell components, cell membranes, spores, DNA, RNA, etc. in a sample fluid comprising for example blood, serum, plasma, saliva, tissue extract, intestinal fluid, cell culture extract, food or feed extract, drinking water, etc. Often a biosensor uses a sensor surface that comprises specific recognition elements for capturing the analyte. The surface of the biosensor device may therefore be modified by attaching specific molecules to it, which are suitable to bind the target molecules to be detected in the sample fluid. A well established principle is the counting of labelled molecules of interest captured at predetermined sites on the biosensor. For example, such molecules of interest may be labelled with magnetic particles or beads and these magnetic particles or beads can be detected with a magnetic sensor. One alternative is detection of the amount of analyte using optical detection such as fluorescence. In this case, the analyte itself may carry a fluorescent label, or alternatively an additional incubation with a fluorescent labelled recognition element may be performed.

In most biosensors, the sensor chip is provided with a dry reagent in addition to the sensor surface. The reagent may e.g. comprise labels coupled to biologically-active moeities, e.g. an anti-drug antibody. In order to limit the analysis time, the reagent can be deposited directly on the sensor surface. When the test fluid arrives, the dry reagent dissolves and mixes into the fluid which will then wet the sensor surface. The labels as well as the sensor surface are exposed to the target, (e.g. drug) molecules. This influences the binding of the labels to the sensor surface, which is detected. An inconvenience of having the reagent deposited directly on the sensor surface is that it leads to possible premature reaction or mixing of the reagent with the sensor surface (i.e. before the reagent has had the possibility to react with the target), thus disturbing the detection.

A bio-sensing system wherein the reagent is physically separated from the sensor surface is disclosed in Fukumoto et al (The 13$^{th}$ International Conference on Solid-State Sensors, Actuators and Microsystems, Seoul, Korea, Jun. 5-9, 2005). In this article, a test cartridge is disclosed comprising a detection chamber equipped with a sensor chip, on which a capture antibody is immobilised, and a cap in which a sample-loading hole is performed. A non-woven fabric, on which detection antibody bound magnetic particles are dotted and freeze-dried, is fixed to the cap in such a way as to cover the hole. A sample including an antigen is then dropped on the cartridge.

SUMMARY OF THE INVENTION

It is an object of the present invention to provide improved systems and methods for detecting an analyte in a sample fluid as well as manufacturing methods for such systems. Advantages of embodiments of the present invention can be speed of measurement (e.g. within one minute), improved timing of measurements, reliability, reproducibility and ease of manufacturing. The above objective is accomplished by a method and device according to the present invention.

In a first aspect, the present invention relates to a device for detecting the presence of an analyte in a sample fluid, the device comprising a detection region being at least partly delimited by a carrier surface accessible to the sample fluid from within the detection region, the carrier surface comprising a reagent, and a sensor surface accessible to the sample fluid from within the detection region, the sensor surface being distinct from the carrier surface, and an inlet for the sample fluid, said inlet for the sample fluid having an inlet opening in the detection region distinct, i.e. remote from the reagent on the carrier surface, i.e. not covered by said carrier surface comprising the reagent. The detection region may be determined by an assembly of surfaces comprising the carrier surface and the sensor surface, without being a closed chamber. The region between the carrier surface and the sensor surface may be free of walls or channels, in other words the region between the carrier surface and the sensor surface may be free of detector parts, e.g. walls. The detection region may be a detection cavity or chamber, e.g. having a fixed volume. The cavity or chamber is bounded by walls. The volume of the cavity or chamber can be optionally fixed after tuning. The latter is e.g. advantageous if a quantitative detection is required. In a detection chamber with fixed volume, a fixed volume of fluid can be provided. A detection chamber is preferred if a competitive assay is performed, as the sample volume is crucial and the concentration of labels determines the result. The number of labels can be defined by providing, e.g. dosing, a well defined volume of a well defined concentration of labels, in combination with a well defined volume resulting in a correct number of labels per volume sample fluid. It is an advantage of embodiments of the present invention that good mixing of the sample fluid with the reagent is obtained. It also is an advantage of embodiments of the present invention that methods and systems can be tuned to the desired mixing and/or reaction time. It furthermore is an advantage of embodiments of the present invention that devices with a long shelf life are obtained. The device may comprise an outlet for fluids.

As an optional feature, the volume of the detection chamber may be comprised between 0.1 µl and 1 µl. This is advantageous because this corresponds to an amount of sample sufficient to perform a proper analysis while at the same time it enables miniaturisation of the device and short detection time.

As an optional feature, the inlet for sample fluid may comprise a capillary. This is advantageous because it enables the transport of fluid, e.g. the sample fluid, via capillary forces, i.e. without requiring additional fluid providing means, such as e.g. pumping means.

As an optional feature, the device may further comprise pressure means for forcing the sample fluid through the inlet for sample fluid. This is advantageous because it permits to cope with sample fluids having a high viscosity.

As an optional feature, the carrier surface is not co-planar with the sensor surface. Preferably, the carrier surface faces the sensor surface. It is an advantage of embodiments of the present invention to reduce and preferably minimise or substantially prevent reaction or mixing between the reagent and the sensor surface. It is an advantage of embodiments of the present invention that independent optimisation of reagent and/or reagent mixing on the one hand and the sensor surface and/or sensor surface reactivity on the other hand can be performed. Furthermore an improved contact between the sample fluid and the sensor surface may be provided.

As an optional feature, the carrier surface delimits one side or part of the detection chamber, e.g. as part of a wall of the chamber. This is advantageous because the carrier surface so fulfils two functions in the device which is economical.

As an optional feature, the carrier surface is non-porous. This is advantageous because it prevents the absorption of sample fluid within said carrier surface which would prevent part of said sample fluid to interact with the reagent. It is an advantage of such embodiments that the carrier surface being non-porous may prevent the sample from being removed from the detection region before detection has taken place.

As an optional feature, the device may further comprise a retention means for retaining the reagent or components thereof on the carrier surface. It is advantageous because it allows the performance of timely defined measurements wherein the time at which the reagent or components thereof have been released is precisely known.

As an optional feature, the device may further comprise an actuation means for moving the reagent or components thereof in the sample fluid. It is an advantage of embodiments of the present invention that both mixing the sample fluid and the reagent or moving components of the reagent to predetermined positions is provided. The actuation and/or retention means may be mechanical devices, pneumatic devices, hydraulic devices, electrical devices, electromagnetic or magnetic retention or actuation means, etc. The latter is advantageous for example if the reagent comprises probes labelled with magnetic or magnetisable particles, as the magnetic actuation means may enable to move those magnetic or magnetisable particles relatively to the sample fluid and/or relative to the sensor surface. This may help improve the mixing of the sample fluid with the reagent and/or the directing of the probes towards the sensor surface, thereby increasing the speed of the detection.

The present invention also provides a device for detecting the presence of an analyte in a sample fluid, the device comprising:

a detection region, the detection region being at least partly delimited by a) a carrier surface accessible to the sample fluid from within the detection region, the carrier surface comprising a reagent, and b) a sensor surface accessible to the sample fluid from within the detection region, the sensor surface being distinct from the carrier surface, and an inlet for the sample fluid, said inlet comprising a capillary.

The present invention also provides a device for detecting the presence of an analyte in a sample fluid, the device comprising:

a detection region, the detection region being at least partly delimited by a) a carrier surface accessible to the sample fluid from within the detection region, the carrier surface comprising a reagent including magnetizable or magnetic entities, and b) a sensor surface accessible to the sample fluid from within the detection region, the sensor surface being distinct from the carrier surface, and c) magnetic retention means for releasably retaining the entities of the reagent on the carrier surface.

It is an advantage of embodiments of the present invention that different components for use in the bio-detection may be provided in a single layer. The applied reagent may comprise one or more probes and/or may be comprised in a soluble material. It is an advantage of embodiments of the present invention that rapid interaction between the sample fluid and the reagent is obtained. For example, upon contact with the sample fluid, the soluble material can be rapidly dissolved. The applied reagent may be comprised in a porous material. This is advantageous because porous materials dissolve faster than non-porous materials.

As an optional feature, the magnetic actuation means may be situated below and/or above the sensor surface. This is advantageous because it enables directing of the probes toward the sensor surface, increasing therefore the rapidity of the detection.

As an optional feature, the reagent may be in a dried or lyophilised form. This is advantageous because this improves the shelf life of the device.

As another optional feature, the reagent may comprise one or more probes. This is advantageous because probes are particularly susceptible to react with the sensor surface and are therefore advantageously physically separated from the sensor surface.

As yet another optional feature, the reagent may be comprised in one or more soluble lyophilised beads. This is advantageous because beads enable an easy quantification of the amount of reagent (e.g. probes) that is provided. As an optional feature, if one or more probes are present, they may be synthetic or natural antibodies or fragments of such antibodies having a binding domain. This is advantageous because it permits to analyse the presence of antigens in a sample fluid.

As another optional feature, the one or more probes may be labelled with magnetic or magnetisable particles. This is advantageous because magnetic labels enable both the detection of the probes and the directing of the probes within the sample fluid.

In a second aspect of the present invention, a process is provided for manufacturing a device for detecting the presence of an analyte in a sample fluid, the process comprising providing a carrier surface, applying a reagent on the carrier surface, providing a sensor surface distinct from the carrier surface, forming a detection region delimited by the carrier surface and the sensor surface, and forming an inlet for sample fluid at a location distinct, i.e. remote from the reagent on said carrier surface. The detection region may be a detection chamber or cavity, e.g. formed by assembling parts of the chamber.

As an optional feature, the applying of the reagent on the carrier surface may comprise any suitable micro-deposition technique such as spotting, pipetting, printing, e.g. non-contact printing such as ink-jet printing, the reagent on the carrier surface. The latter is advantageous because printing, preferably ink-jet printing, is a precise and flexible way to deposit the reagent, especially small amounts of reagents. Another advantageous micro-deposition technique is the use of a dosing equipment using valves instead of piezoelectric elements to dose about 100-500 nl of reagent.

As another optional feature, the applying of the reagent on the carrier surface may further comprise drying the reagent. This is advantageous because it improves the shelf life of the device which may therefore be stored without influence on its efficiency.

As another optional feature, the applying of the reagent on the carrier surface may further comprise freeze-drying the reagent. This is advantageous because this is a particularly efficient drying process.

As another optional feature, the process for manufacturing a device for detecting the presence of an analyte in a sample fluid may further comprise providing magnetic actuation means below and/or above the sensor surface. This is advantageous because it enables directing of the probes toward the sensor surface, increasing therefore the rapidity of the detection.

As another optional feature, the process for manufacturing a device for detecting the presence of an analyte in a sample fluid may further comprise providing magnetic retention means below and/or above the carrier surface. This is advantageous because it enables to timely control the release the reagent or components thereof.

As another optional feature, the distance between the carrier surface and the sensor surface may be tuned. This is advantageous because it allows well defined and reproducible analysis times.

As another optional feature, forming a detection region may comprise assembling a detection chamber using the sensor surface and the carrier surface, after applying the reagent. This is advantageous because it enables an easier application of the reagent as a consequence of the better availability of the carrier surface. As another optional feature, the method may comprise applying the reagent on the carrier surface after the detection region, e.g. detection chamber, has been formed.

In a third aspect of the invention, a method is provided for detecting the presence of an analyte in a sample fluid, the method comprising:

providing the sample fluid via an inlet for sample fluid in the detection region, the inlet for sample fluid having an inlet opening, contacting the sample fluid with a reagent present on said carrier surface delimiting the detection region, the reagent being positioned distinct, i.e. remote from the inlet opening, thereby forming a fluid mixture, the carrier surface being accessible to the sample fluid from within the detection region, contacting the fluid mixture with a sensor surface, the sensor surface being distinct from the carrier surface, and detecting the interaction between the fluid mixture and the sensor surface. The detection region thus may be a detection chamber or cavity. The detection region may be delimited by the carrier surface.

One or more probes labelled with magnetic or magnetisable particles may be provided within the sample fluid. As an optional feature, the reagent, comprising magnetic or magnetisable particles can be placed accurately by directing it towards the carrier surface by using magnetic actuation. As another optional feature, the method may further comprise the step of magnetically actuating the magnetic or magnetisable particles before the detecting. For instance, the step of magnetically actuating the magnetic or magnetisable particles may be performed in order to direct the magnetic or magnetisable particles toward the sensor surface. This is advantageous because it increases the speed of analysis.

As another optional feature, the step of magnetically actuating the magnetic or magnetisable particles may be performed in order to mix the probes with the sample fluid. This has the advantage to increase the reproducibility of the analysis.

As another optional feature, the step of magnetically retaining the magnetic or magnetisable particles may be performed in order to control their time of release.

Contacting the sample fluid may be provided by dipping an assembly comprising the carrier surface and the sensor surface in the sample fluid.

These and other aspects of the invention will be apparent from and elucidated with reference to the embodiment(s) described hereinafter.

Particular and preferred aspects of the invention are set out in the accompanying independent and dependent claims. Features from the dependent claims may be combined with features of the independent claims and with features of other dependent claims as appropriate and not merely as explicitly set out in the claims.

The teachings of the present invention permit the design of improved methods and apparatus for detecting analytes in a sample fluid.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1A:
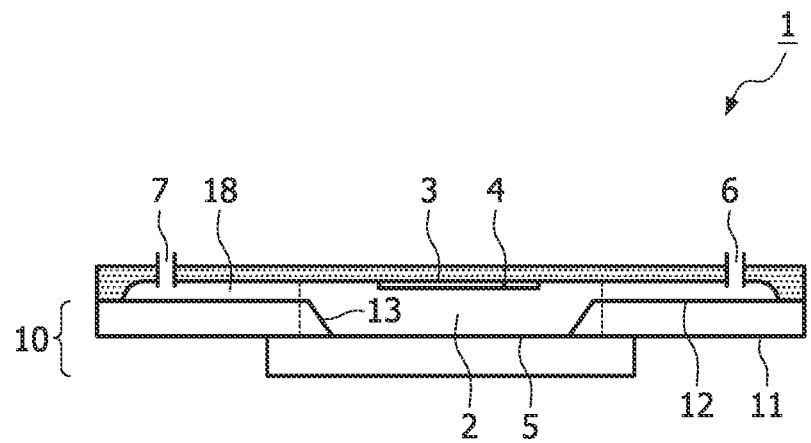
FIG. 1a is a schematic representation of a part of a device for sensing according to one embodiment of the present invention.

In the different figures, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

Reference throughout this specification to "one embodiment" or "an embodiment" means that a particular feature, structure or characteristic described in connection with the embodiment is included in at least one embodiment of the present invention. Furthermore, the particular features, structures or characteristics may be combined in any suitable manner, as would be apparent to one of ordinary skill in the art from this disclosure, in one or more embodiments. The claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art.

The following terms or definitions are provided solely to aid in the understanding of the invention. The definitions should not be construed to have a scope less than understood by a person of ordinary skill in the art.

The term "sample", as used herein, relates to a composition which may comprise at least one analyte of interest. The sample is preferably fluid, also referred to as "sample fluid", e.g. an aqueous composition. The term "analyte", as used herein, refers to a substance whose presence, absence, or concentration is to be determined by using embodiments of the present invention. Analytes may include, but are not limited to organic molecules, metabolites such as glucose or ethanol, proteins, peptides, nucleic acid segments, molecules such as pharmaceuticals, antibiotics or drugs, drugs of abuse, molecules with a regulatory effect in enzymatic processes such as promoters, activators, inhibitors, or cofactors, viruses, bacteria, cells, cell components, cell membranes, spores, DNA, RNA, micro-organisms and fragments and products thereof, or any substance for which attachment sites, binding members or receptors (such as antibodies) can be developed. The term "label", as used herein, refers to a molecule or material capable of generating a detectable signal or capable of binding to another molecule or forming a complex which generates a detectable signal. Suitable labels for use in different detection systems and methods of the present invention are numerous and extensively described in the art. These may be optical labels (e.g. luminescent molecules (e.g. fluorescent agents, phosphorescent agents, chemiluminescent agents, bioluminescent agents and the like), coloured molecules, molecules producing colours upon reaction), radioactive labels, magnetic and/or electric labels, enzymes, specifically bindable ligands, microbubbles detectable by sonic resonance and the like. Labels can be direct labels, which can be detected by a sensor. Alternatively, labels can be indirect labels, which become detectable after a subsequent development process. The label used in the methods of the present invention may be an analyte-specific label, i.e. capable of binding specifically to the analyte. Nevertheless, it is also envisaged that where the analyte is present in a purified form, it is sufficient that the label binds to the analyte.

The term "analyte analogue", as used herein, refers to a substance that can associate with a probe or capture probe less optimally than the analyte. The analyte analogue is used in competitive assays where the analyte is determined based on competition with the analyte analogue, e.g. in the competitive binding to a probe or capture probe. In particular, the analyte analogue binds to a probe or capture probe with a reduce binding strength compared to the binding of the analyte to a probe or capture probe. The term "probe" relates in the present invention to a binding molecule that specifically binds an analyte. Probes envisaged within the context of the present invention include biologically-active moieties such as but not limited to whole anti-bodies, antibody fragments such as Fab' fragments, single chain Fv, single variable domains, VHH, heavy chain antibodies, peptides, epitopes, membrane receptors or any type of receptor or a portion thereof, substrate-trapping enzyme mutants, whole antigenic molecules (haptens) or antigenic fragments, oligopeptides, oligonucleotides, mimitopes, nucleic acids and/or mixture thereof, capable of selectively binding to a potential analyte. Antibodies can be raised to non-proteinaceous compounds as well as to proteins or peptides. Probes may be members of immunoreactive or affinity reactive members of binding-pairs. The nature of the probe will be determined by the nature of the analyte to be detected. Most commonly, the probe is developed based on a specific interaction with the analyte such as, but not limited to, antigen-antibody binding, complementary nucleotide sequences, carbohydrate-lectin, complementary peptide sequences, ligand-receptor, coenzyme, enzyme inhibitors-enzyme, etc. In the present invention, the function of a probe is specifically interact with an analyte to permit its detection. Therefore, probes may be labelled or may be directly or indirectly detectable. The probe can be an anti-analyte antibody if, for instance, the analyte is a protein. Alternatively, the probe can be a complementary oligonucleotide sequence if, for instance, the analyte is a nucleotide sequence. The term "capture probe" as used herein, refers to probes for immobilizing analytes and/or labelled analytes on a sensor surface via recognition or binding events. The term "sensor" as used herein, refers to a device allowing qualitative and/or quantitative detection of an analyte in a sample fluid. If the analyte is of biological nature or if the sensor relies on biological entities for the detection, (e.g. antibodies capture probes) the sensor will sometimes be referred as a "biosensor". The "sensor" as used herein usually operates its sensing through a sensing surface that will either capture analytes or exchange an analyte analogue immobilized thereon for an analyte present in the sample fluid.

In a first aspect, the present invention relates to a device for detecting the presence of an analyte in a sample fluid, the device comprising a detection region. The detection region is at least partly delimited by a carrier surface accessible to the sample fluid from within the detection region. The carrier surface may e.g. be part of a detection chamber or cavity, e.g. forming one of the walls or being on the roof thereof although the carrier surface also may be provided as an additional surface in the detection chamber. The detection region is further delimited by a sensor surface distinct from the carrier surface. The sensor surface is accessible to the sample fluid from within the detection region. The sensor surface may e.g. be part of the same detection chamber. The detection region may be determined by an assembly of surfaces comprising the carrier surface and the sensor surface, without being a closed chamber. The region between the carrier surface and the sensor surface may be free of walls or channels, in other words the region between the carrier surface and the sensor surface may be free of detector parts, e.g. walls. The detection region may be a detection chamber, e.g. having a fixed, optionally fixed after tuning, volume. The latter is e.g. advantageous if a quantitative detection is required. In a detection chamber with fixed volume, a fixed volume of fluid can be provided. Preferably, the volume of the detection chamber is comprised between 0.1 and 1 µl. The device further comprises an inlet for the sample fluid. The inlet for the sample fluid has an inlet opening in the detection region distinct, i.e. remote from the reagent on the carrier surface, e.g. not covered by the carrier surface. The inlet for the sample fluid may comprise a capillary, e.g. a tube or a hollow section with dimensions such that liquid, e.g. a liquid sample fluid, can be driven therein via capillary forces. Typical dimension for capillary sections are 0.1 to 2 mm. The device may further comprise pressure means for forcing the sample fluid through the inlet for sample fluid. Suitable pressure means comprise but are not limited to e.g. pumps, syringe and the likes. The pressure exerted by said pressure means can be positive or negative, e.g. vacuum, i.e. a negative pressure, may be applied at an outlet for fluid of said device. A detection chamber with well-defined volume also is preferred if a competitive assay is performed, as the sample volume is crucial and the concentration of labels determines the result. The number of labels can be defined by providing, e.g. dosing, a well defined volume of a well defined concentration of labels, in combination with a well defined volume resulting in a correct number of labels per volume sample fluid. The substrate of the carrier surface and of the sensor surface can be identical or different in nature. The nature of the material is not a limiting feature of the present invention. The materials can be made of any suitable substrate material, such as but not limited to a flexible organic material, e.g. a polymeric material, such as polyester, especially high temperature polyester materials, polyethylene naphtalate (PEN), and polyimide, or mixtures of two or more of these. Another possible material is an inorganic material, for example a semiconductor material such as e.g. silicon, or a glass type material such as e.g. glass or quartz. The carrier surface is preferably non-porous, i.e. not prone to absorb liquids within said surface.

The sensor surface may also be constituted by the solid surface of a detection surface of the detector used. The detector used may for example be an optical detector, a magnetic detector, a mechanical detector, etc. the invention not being limited thereto. The sensor surface preferably comprises biologically or biochemically active moieties for capturing particles of interest. Biologically or biochemically active moieties may for example refer to capture probes and/or analyte analogs that are attached to the sensor surface and that are capable of binding, or that are reactive with, an analyte or labelled probe, respectively, when in appropriate conditions. The capture probes and/or analyte analogs of the biologically-active layer may be retained or immobilized on the surface by any method known in the art. These biologically-active moieties may be attached to the detection surface in a site-specific manner meaning that the specific sites on these moieties are involved in the coupling, e.g. through a protein-resistant layer on the surface. The sensor surface may have a porous surface in order to enhance the surface-over-volume ratio.

The carrier surface comprises a reagent, e.g. the carrier surface has a reagent applied on its surface. The reagent is preferably a dissolvable reagent, i.e. a reagent adapted for dissolving once in contact with the sample fluid. The reagent may be assisting in label-based analyte detection. It may comprise reagents of chemical or biochemical nature for reacting with the analyte to produce a detectable signal that represents the presence of the analyte in the sample. For instance, the reagent may comprise a probe or a labeled probe. In a particular embodiment, the reagent comprises probes labeled with magnetic or magnetisable particles. Suitable reagents for use in different detection systems and methods include a variety of active components selected to determine the presence and/or concentration of various analytes. There are numerous chemistries available for use with each various analytes. They are selected with respect to the analyte to be assessed. In one example, the probe comprised in the reagent is an anti-body. In other examples, the reagent may contain for example an enzyme, a co-enzyme, an enzyme inhibitor, an enzyme substrate, a co-factor such as ATP, NADH, etc. to facilitate enzymatic conversion, a vitamin, a mineral, the invention clearly not limited thereto. The reagent may be applied by way of a layer applied to the carrier surface. For example, in one preferred embodiment, the at least one reagent layer can include one or more enzymes, co-enzymes, and co-factors, which can be selected to determine the presence of metabolites or small molecules in a sample. Furthermore, the reagent may also comprise labels, buffer salts, detergents, sugars, etc.

As an optional feature, the reagent may be in a dried or lyophilized form. This results in a long shelf life, i.e. good properties during storing whereby e.g. interaction prior to addition of sample fluid is limited. In one particular embodiment, the reagent is comprised in a porous material, e.g. it forms a porous layer. The latter is obtained by depositing a reagent layer comprising material that sublimes during drying and by drying the reagent layer, e.g. sublimation of water and/or of a salt such as ammonium carbonate. The porous reagent layer thus obtained furthermore may be nano-porous or micro-porous. Porosity is advantageous as it assists in improving dissolving of the reagent components. In another particular embodiment, the reagent is comprised in one or more soluble lyophilised beads. These beads can be formed, for example, by dropping a solution containing the constituents of the reagent in a freezing medium, followed by freeze drying the obtained beads. The reagent may be applied by any suitable micro-deposition technique such as spotting, pipetting, printing, e.g. ink-jet printing at the appropriate position in the device for detecting, as will be described in more detail below. In still another embodiment, more than one reagent layer can be deposited on top of each other and/or on different carrier surfaces in the device for detecting, e.g. beside each other.

As an optional feature, the carrier surface may be situated above the sensor surface. In some embodiments of the present invention, the carrier surface comprises the roof of the detection region, e.g. detection chamber, or is on the roof thereof. For instance, the carrier surface may delimit a the top side, of the detection region, e.g. detection chamber. In a particular embodiment, the detection region, e.g. detection chamber may be formed of the assembly of a sensor supporting element on one hand and a lid comprising the carrier surface on another hand, which will be described in more detail with regard to FIG. 2a to FIG. 5b. Alternatively, the carrier surface may be situated between the sensor surface and the surface delimiting the opposite side of this region, e.g. chamber (i.e. the roof of the chamber). In such a case, a support is provided to the carrier surface in order to immobilise the carrier surface in this position. It is also possible to realise a detection region, e.g. detection chamber having two or more carrier surfaces each of them carrying a reagent.

The distance between the carrier surface and the sensor surface may be selected such that at least a minimal interaction or mixing time occurs before the components of the sample interacted with the reagent reaches the sensor surface. In this way, the interaction or mixing time between the sample fluid and the reagent may be selected or tuned. An aspect of the present invention is to provide a distance between the carrier surface and the sensor surface such that an interaction time of at least 1 second and preferably an interaction time in the range of 5 to 60 seconds is provided. This time can be tuned e.g. by changing the distance carrier surface-sensor or changing the magnetic force for a given distance. Another aspect of the present invention is to provide a tunable distance, e.g. a mechanically or electro-mechanically tunable distance, between the carrier surface and the sensor surface. Such tunable parts may e.g. be obtained using micro-electro-mechanical systems (MEMS), the invention not being limited thereto. By way of example, standard and optional components of an exemplary part of a device for detecting are shown in FIG. 1a, embodiments of the present invention not being limited thereto. FIG. 1a shows a schematic cross section of a device 1 for detecting, the device 1 comprising a detection region 2, by way of illustration being a detection chamber 2, in the present example illustrated in the middle of device 1. The detection region 2 is delimited on its top side by a carrier surface 3 and on its bottom side by a sensor surface 5 attached on an first side 11 of an optional sensor supporting element 10. The carrier surface 3 according to the present embodiment comprises a reagent 4 applied thereon. The detection region 2 in the present embodiment is shown nominally delimited on its left side and its right side by dashed lines. In the present example, on the left and the right side of the detection chamber 2, optional sloped walls 13 of the sensor supporting element 10 are shown. The left side and the right side of the detection region 2 are not fully delimited by the sloped walls 13 of the sensor supporting element 10 in order to enable a fluidic connection between the detection region 2 and a fluidic channel 18 formed between the second side 12 of the sensor supporting element and the carrier surface 3. The fluidic channel 18 is represented connected to an inlet 6 for sample fluid 20 and an outlet 7 for removing the resulting fluid.

Figure 1B:
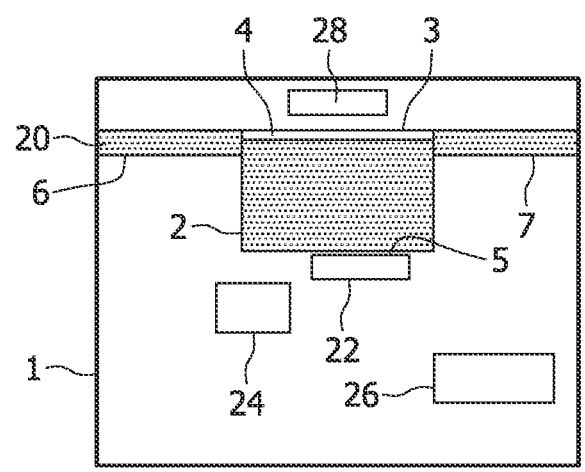
FIG. 1b is a schematic representation of a device for sensing according to embodiments of the present invention.

A schematic representation of a device for detecting is shown in FIG. 1b, indicating standard and optional parts of the device. The device 1 comprises a detection region 2 with a carrier surface 3 comprising reagent 4 and a sensor surface 5 distinct from the carrier surface. These components may e.g. be as shown in FIG. 1a, although the invention is not limited thereto. A device 1 for detecting according to the present invention furthermore may comprise a detection means 22 for detecting a signal representative of the presence and/or amount of analytes present in the sample fluid 20. The detecting means 22 may be located inside the detecting chamber or it may be located outside thereof. Access for the detecting means may be provided by a transparent window in the detecting chamber.

Further an excitation means 24 may be provided for example for exciting labels assisting in the detection. The detection means 22 may include any suitable detector, e.g. a magnetic or optical detector, although the invention is not limited thereto. The magnetic detector may for example be a Hall detector or may include a magneto-resistive element such as a GMR, TMR or AMR sensor. The device 1 for detecting furthermore may comprise a processing means 26 for processing the detector results thus allowing to provide a suitable output. Such processing means 26 may be any suitable means such as for example a computing means. The device 1 also may comprise a fluid inlet 6 and/or a fluid outlet 7. In some embodiments, the use of the fluid inlet 6 is for serving as an entry port for the sample fluid 20. As an optional feature, the device may further comprise retention means 28 for retaining the reagent 4 or components thereof on the carrier surface 3. Such retention means should be able to both hold the reagent 4 or components thereof on the carrier surface 3 and release the reagent 4 or components thereof from the carrier surface 3. A non-limiting example of retention means may be a magnetic retention means comprising but not limited to permanent magnets, electromagnets, coils, etc. in the case of a reagent comprising magnetic or magnetisable particles. Such a retention means is preferably placed above the carrier surface. Such a retention means can be used to release the reagent or components thereof at a chosen time in order to performed timely controlled measurements. The magnetic retention means may be switchable or permanent. The magnetic retention means also may be e.g. mechanical retention means. The retention means may also be located outside of the detection region.

As an optional feature, according to some embodiments of the present invention, the device 1 further may comprise actuation means 28. The actuation means 28 may be a mixing means and/or may be a means for positioning or displacing components of the fluid mixture, e.g. after contacting the sample fluid 20 with the reagent 4. The actuation means may be used for actuation of magnetically labeled probes optionally present in the reagent 4. The actuation means 28 therefore may be a magnetic actuation means comprising but are not limited to permanent magnets, electromagnets, coils, etc. Preferably, the actuation means 28 are situated below and/or above the sensor surface 5. Preferably, magnetic actuation means are present below the sensor surface and optionally also above the sensor surface. The magnetic actuation means may be switchable or permanent. The actuation means also may be electrical actuation means or mechanical or acoustical actuation means. The actuation means may also be located outside of the detection region.

With respect to FIGS. 2a to 5b, a preferred embodiment of a device 1 for detecting, wherein the carrier surface 3 with the reagent 4 is provided on a lid 8 forming a side top or wall, e.g. roof, of the detection region 2. The latter allows separate manufacturing of a component for the device 1 comprising the carrier surface 3 and a component for the device 1 comprising the sensor surface 5. This therefore allows independent manufacturing, thus resulting in independent degrees of freedom for manufacturing these components. By way of illustration, the present invention and the preferred embodiment, not being limited thereto, an example of such an embodiment is shown in FIG. 2a to FIG. 5b.

Figure 2A:
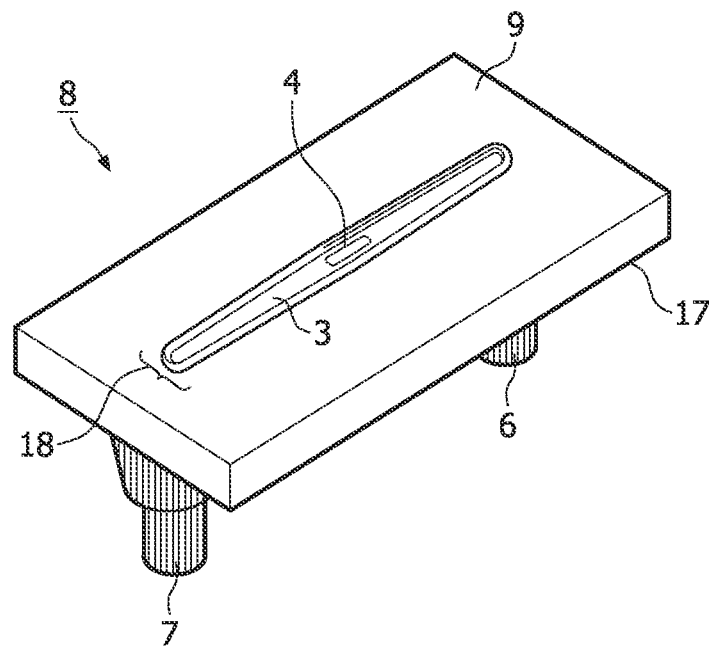
FIG. 2a and FIG. 2b show a top view of a front and bottom side of a lid comprising a carrier surface with reagent according to a preferred embodiment of the present invention.
Figure 2B:
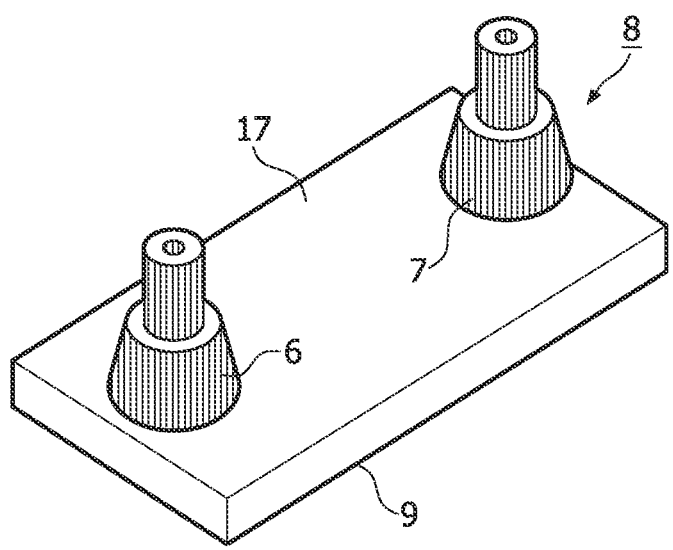
Figure 3A:
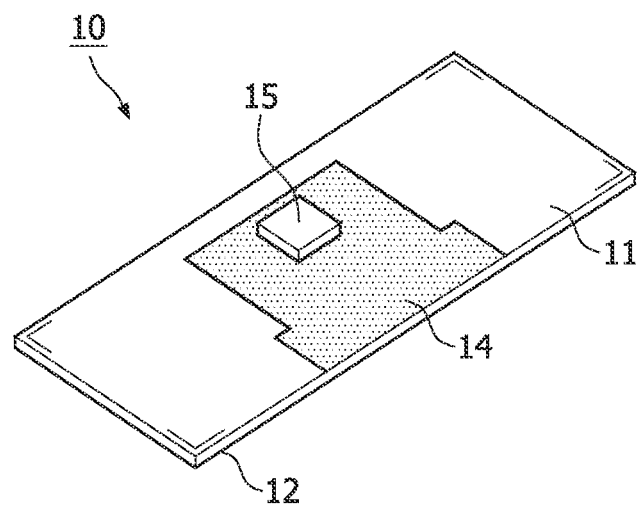
FIG. 3a and FIG. 3b show a top view of a front and bottom side of a sensor supporting element according to a preferred embodiment of the present invention.
Figure 3B:
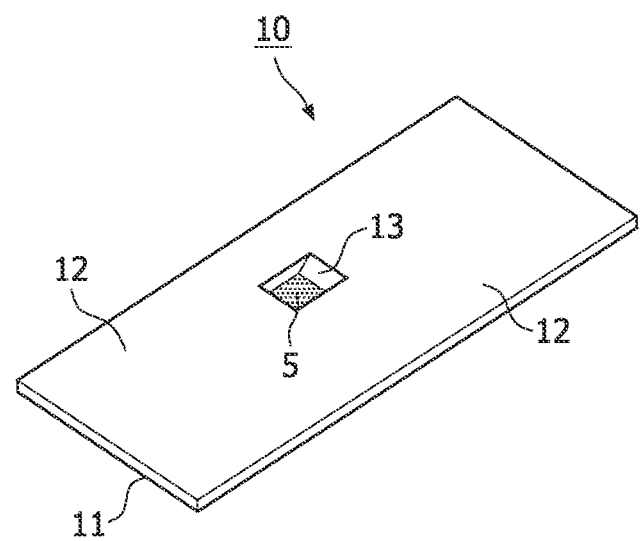
Figure 4A:
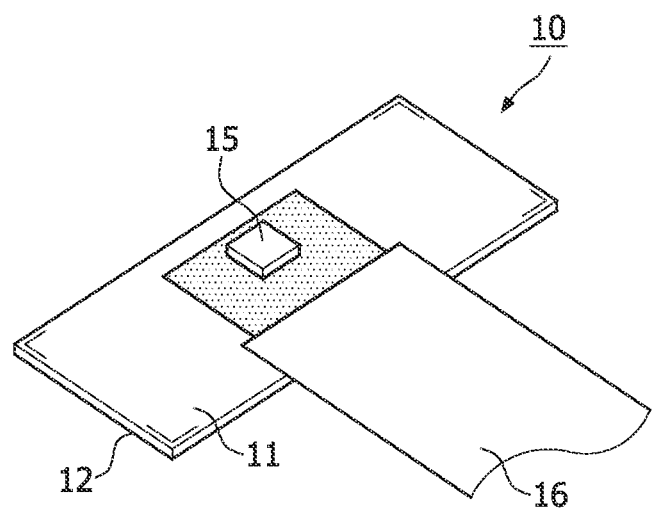
FIG. 4a and FIG. 4b show a top view of a front and bottom side of a sensor supporting element with connection means according to a preferred embodiment of the present invention.
Figure 4B:
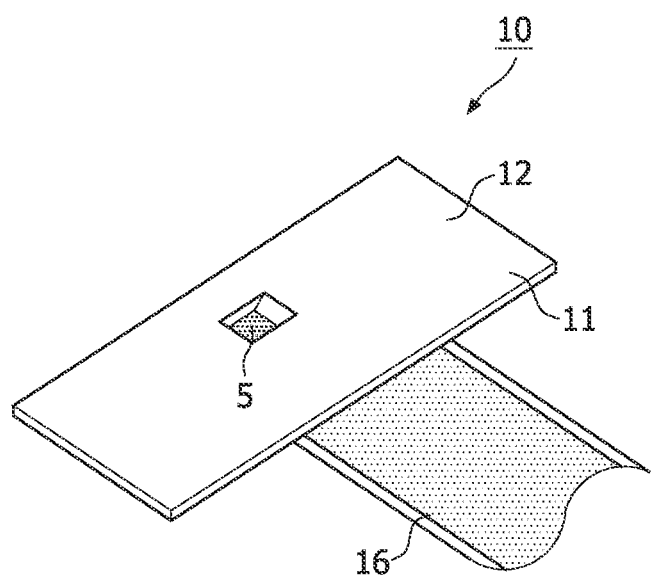
Figure 5A:
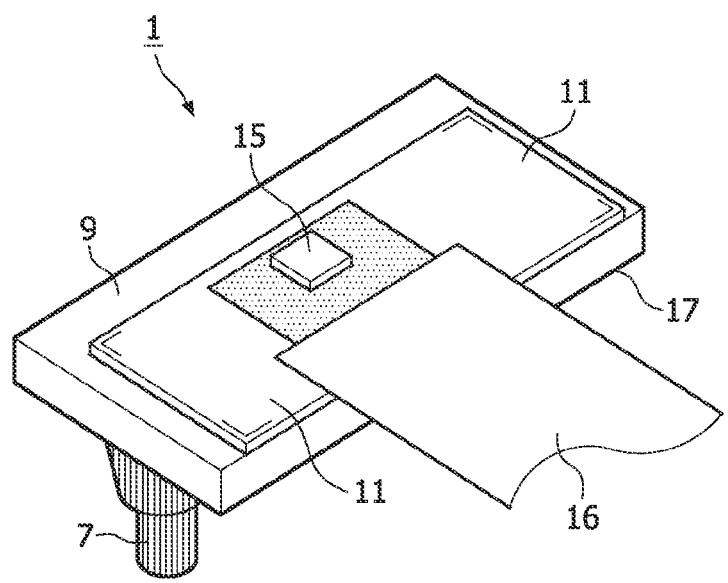
FIG. 5a and FIG. 5b show a top view of a front and bottom side of a sensor device according to a preferred embodiment of the present invention.
Figure 5B:
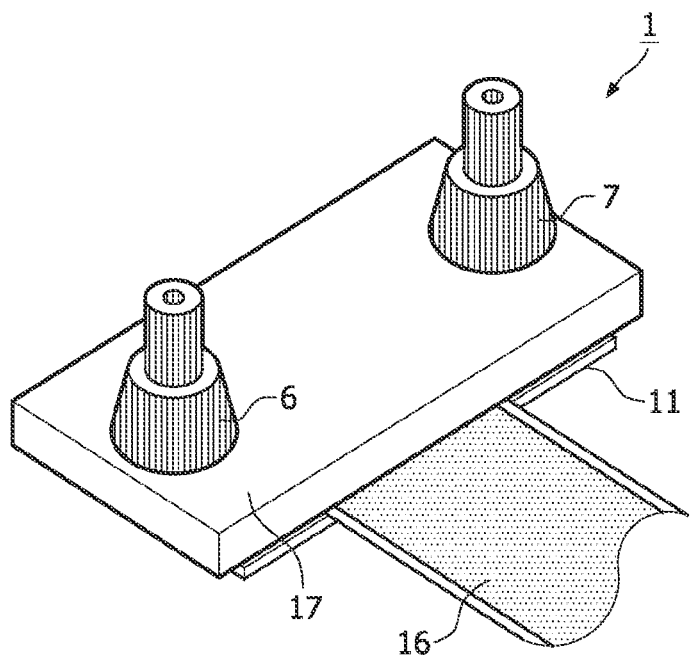

FIG. 2a shows a component of the device 1 comprising the carrier surface 3, i.e. on or in a lid 8, from a first side 9 in top view. In the present example, the lid 8 is provided with a channel 18 delimited by the carrier surface 3 on its bottom side and open on its top side. The carrier surface 3 comprises a reagent 4 applied on a central portion thereon. The lid 8 can be provided with an inlet for fluids 6 and an outlet for fluids 7. FIG. 2b shows, in top view, the same lid 8 from an opposite second side 17. FIG. 3a shows, in top view, a component of the device 1 comprising the sensor surface 4 on the first side 11 on which a sensor 15 is attached, i.e. a sensor supporting element 10. The sensor supporting element 10 thus has a first side 11, whereon e.g. tracks may be presents and a second side 12. FIG. 3b shows, in top view, the second side 12 of a sensor supporting element 10. An opening is shown for providing connection between the second side 12 of the sensor supporting element and the sensor surface 5. The opening is shown having sloped walls 13. FIG. 4a and FIG. 4b show, in top view, the sensor supporting element 10 after the provision of a connection means 16 for external contacting, e.g. a flex foil 16 for external contacting. FIG. 5a and FIG. 5b show the device 1 after assembly of lid 8 and the sensor supporting element 10, in top view, from the first side 11 of the supporting element 10 respectively from the second side 17 of the lid 8. To provide the lid 8 on the second side 12 of the sensor supporting element, use is made, for example, of an adhesive.

In a second aspect, the present invention relates to a process for manufacturing a device 1 for detecting the presence of an analyte in a sample fluid 20. The device may be a device as described in the first aspect of the present invention, comprising the same features and advantages. The process comprises applying a reagent 4 on a carrier surface 3. The reagent 4 may be deposited in any suitable way, such as but not limited to e.g. micro-deposition techniques. One example of deposition is dosing, whereby valves are used to control application of small volumes on the carrier surface. Other techniques may comprise non-contact printing techniques such as inkjet printing or jetting, or contact printing such as tampon printing, micro contact printing, screen printing, stamp printing, etc. The reagent 4 may for instance be deposited as one or more layers.

As an optional feature, the reagent 4 may be dried on the carrier surface 3. Drying of the reagent on the carrier surface 3 may be performed by application of a low ambient vapour pressure, although the latter is not obligatory. Drying may comprise both drying a reagent 4 from its fluid phase as well as drying a reagent 4 from its solid phase. It may comprise reducing the amount of aqueous components present in the reagent 4. Heat may be used during drying to improve its efficiency. For instance, the carrier surface 3 may be heated. A good drying improves shelf life, i.e. storage properties. In an exemplary embodiment, the ambient provided during depositing and/or drying of the reagent 4 has a very low humidity. The latter has the advantage that the drying proceeds rapidly. An inert gas can be used in the ambient. With very low humidity there is meant a relative humidity less than 30%, more preferably a relative humidity less than 10% and even more preferably a relative humidity of less than 3%. As an optional feature, the reagent 4 may be in a lyophilised form, i.e. has been freeze-dried by first freezing it and afterwards subliming the frozen water formed therein. In other words, a step of lyophilizing also may be applied.

The process of this second aspect further comprises providing a sensor surface 5 distinct from the carrier surface 3. The sensor surface 5 may be obtained pre-made whereon biologically or biochemical active moieties are already provided, or it may be obtained via the coating of a sensor or sensor surface with biologically or biochemical active moieties. The process of this second aspect further comprises forming a detection region delimited by the carrier surface 3 and the sensor surface 5, e.g. forming a detection chamber comprising the carrier surface 3 and the sensor surface 5. Such an assembly of a detection chamber may be performed by positioning the different components in their appropriate position and fixing the components to each other. The latter may be performed in any suitable way, e.g. by glueing, clipping, clicking, welding etc. Further assembly of the device for detecting also may be performed, i.e. for example providing a detection means, providing a connection means for connecting the detection means obtaining a read-out of the detection means used. The assembly, i.e. forming the detection region, may be performed after the reagent has been applied to the carrier surface or it may be performed prior to applying the reagent on the carrier surface. For instance, the reagent may be introduced via openings performed in the device. An advantage of separate manufacturing the sensor surface and the reagent applied to the carrier surface and thereafter assembling is that independent optimization of the preparation may be performed and thus less unwanted cross-interaction between both components occurs. The process of this second aspect of the present invention further comprises providing an inlet and/or an outlet for sample fluid at a location distinct, i.e. remote from the carrier surface. Those inlet and or outlet can be formed by any way known to the person skilled in the art such as drilling, boring, punching, cutting, inserting an object, e.g. an hollow tube, and the likes.

As an optional feature, the distance between the carrier surface and the sensor surface may be tuned during manufacturing. This distance should be such as to provide enough time for a proper dissolution of the reagent by the sample fluid and for a proper homogenisation of the resulting fluid mixture and to provide for rapid detection. A compromise must therefore be found.

As an optional feature, the process of this second embodiment further comprises providing magnetic actuation means below and/or above the sensor surface. Such actuation means may be embedded in a component, or may be positioned as separate component. It may be performed as part of the assembly of the detection chamber or it may be provided after assembly of the detection chamber.

In a third aspect, the present invention, relates to a method for detecting the presence of an analyte in a sample fluid 20. The method preferably may be performed using a device 1 for detecting as described in the first aspect, although the invention is not limited thereto. The method for detecting comprises contacting the sample fluid 20 with a reagent 4 present on a carrier surface 3 thereby forming a fluid mixture, the carrier surface delimiting a detection region 2. In this way analytes present in the sample fluid 20 may interact with the reagent 4, thus assisting in the detectability of the particles of interest. This contacting step may comprise dissolving a dissolvable matrix wherein reagent components are positioned, e.g. dissolving a reagent layer applied to a carrier surface 3. Once the reagent 4 is contacted with the sample fluid 20, e.g. lyophilised beads of reagent, when used, dissolve and liberate their content. Thereafter, the so formed fluid mixture is contacted with the sensor and wet its surface. The method thus furthermore comprises contacting the fluid mixture with a sensor surface, the sensor surface 5 being distinct from the carrier surface 3 and delimiting the detection region 2. In this way interaction between the particles of interest and the sensor surface 5 is obtained. Such an interaction can be performed rapidly as the sensor surface 5 is initially substantially free of reagent 4, thus resulting in free areas of interaction for the particles of interest. The detection region 2 may be a detection chamber 2 comprising the carrier surface 3 and the sensor surface 5. Furthermore, as the reagent 4 is provided in the detection region 2, provision of the reagent 4 sufficiently close to the sensor surface 5 assists in a rapid interaction. The method furthermore comprises detecting the interaction between the fluid mixture and the sensor surface. The latter allows to obtain a quantitative or qualitative analysis of the sample fluid, e.g. to obtain information about the presence and quantity of certain components in the sample fluid. The detection of the interaction of the fluid mixture the sensor surface may comprise the detection of the analyte via detection of the probes. The probes (e.g. the labeled antibodies) and the sensor are both exposed to the analyte and the analyte influences the binding of the probes to the sensor surface. Depending on the type of assay being performed, an analyte labeled with e.g. a magnetic or magnetisable particle (via a probe) either bind to immobilised capture probes (sandwich assay), or compete with analyte analogues to bind to capture probes (competitive assay). After removal of excess (unbound) labeled probes (which in some embodiments is equivalent with the removal of the magnetic or magnetisable particles), the amount of bound labeled probes (e.g. labeled with magnetic particles) can be measured. Thus, binding assays may involve adherence of magnetically labeled molecules to the sensor in numbers that reflect the concentration or presence of the analyte molecule. Such tests may e.g. be used for detecting drugs of abuse, although the invention is not limited thereto. A large number of variations on binding assay methodologies have been described and are all within the scope of the present invention. Detection of a magnetic or magnetisable particle when used as a label is generally done by application of an electric, or magnetic, or electromagnetic field and using a magnetic or non-magnetic, e.g. optical or acoustic sensor. Examples of embodiments for the detection of a magnetic or magnetisable particle are given in patent application WO2005/116661 and in references cited therein. Acoustic and/or sonic detection of labels may also be used. In some embodiments, the magnetic particles are only presents in the lyophilised beads to enable their manipulation via magnetic means, i.e. magnetic actuation and do not serve as labels. In those embodiments, the detection of the probes on or in the sensor will be adapted to the type of label linked to the probes. Also, the various types of binding and releasing assays may use magnetic particles that comprise optical properties such as e.g. fluorescent, chromogenic, scattering, absorbing, refracting, reflecting, SERRS-active or (bio) chemiluminescent labels, molecular beacons, radioactive labels, or enzymatic labels. Optically active labels may emit light detectable by a detector, e.g. in the visual, infrared or ultraviolet wavelength region. Nevertheless, the invention is not limited thereto and optical labels, in the present application, may refer to labels emitting in any suitable and detectable wavelength region of the electromagnetic spectrum.

In some embodiments, contacting the carrier surface with the sample fluid may be obtained by dipping the assembly of carrier surface and detection surface in the sample fluid. The time required to perform an analysis from the sample fluid injection to the detection of the analyte may be tuned. For instance, this time can be selected or tuned by varying the height of the detection region, e.g. detection chamber. Preferably, the height of the chamber can be selected or tuned between 30 µm-500 µm. This can be performed during manufacturing or after manufacturing. For tuning the distance between the carrier surface and the sensor after manufacturing, displacement means, such as for example mechanical, electromechanical or electromagnetic displacement means, may be provided to control the distance between the carrier surface and the sensor, thus allowing to tune the distance between the carrier surface and the sensor. Such tunable parts may e.g. be obtained using micro-electromechanical systems (MEMS), the invention not being limited thereto. This time will also vary in function of the nature and the state of the reagent. This can for instance be tuned by choosing an appropriate drying buffer if the reagent is applied from a buffer solution.

The time required to perform an analysis, i.e. the mixing time of the reagent and the sample fluid and the time between the mixing and detection, also may be tuned by actuating components of the reagent once they have mixed with the sample fluid. The actuating may comprise mixing components of the reagent in the sample fluid or displacing components or bound components towards the sensor surface. Such actuating may be actuating using magnetic force, using electric force, using mechanical or acoustical force, etc. If for example magnetic particles or beads are used to label probes present in the reagent magnetic actuation may be used. A step of magnetically actuating the magnetic or magnetisable particles may thus be performed in order to direct the magnetic or magnetisable particles toward the sensor surface. Alternatively or in addition thereto, a step of magnetically actuating the magnetic or magnetisable particles may be performed in order to mix the probes with the sample fluid. Alternatively or in addition thereto, a step of magnetically retaining the magnetic or magnetisable particles may be performed in order to control the time of their release. The magnetic properties of the magnetic beads or particles and the strength of the magnetic field used may be used to influence on the pre-incubation time. Magnetic forces can for example be tuned by tuning the strengths of the permanent magnets or their distance to the measurement chamber, or in case of electro-magnets they can be tuned by tuning the current through the coils. Appropriate strength for the magnetic field are in the range 0.05 T and above, preferably between 0.05 and 1 Tesla. The size of the magnetic beads is another parameter that influence this time. Preferred sizes for magnetic beads or particles range between 200 nm and 1 µm.

By tuning magnetic forces and the height of the measurement chamber a well-defined and reproducible incubation time can be enforced, resulting in good detection systems and methods.

In one particular example, the method thus comprises magnetically actuating the magnetic or magnetisable particles prior to detecting. The magnetically actuating may e.g. be performed using a magnetic actuation means below the sensor surface. The use of magnetic actuation means below the sensor surface enables to direct the magnetic labels toward the sensor surface at relatively high speed. By way of example, the presence of magnetic actuation means both below and above the sensor surface enables, if at least one of those actuation means is switchable, to improve the contacting of the magnetically labeled probes with the analyte, i.e. the mixing, by either alternatively switching the magnetic actuation means situated above and under the sensor surface or intermittently switching or decreasing/increasing the power of magnetic actuation means situated above or under the sensor surface.

The magnetic force on a magnetic label is given by formula one:

$$F_M = \mu_0 \frac{d}{dx}(H \cdot M) = \mu_0 \chi \frac{d}{dx}|H|^2 \quad (1)$$

where H is the magnetic field strength, $\mu_0 \approx 4\pi 10^{-7}$ the magnetic permeability in vacuum and $\chi$ is the magnetic susceptibility ($\approx 2.5$ for super-paramagnetic beads) and M is the overall magnetisation on the label. The friction force on a bead is given by equation 2:

$$F_w = kv = 6\pi\eta r v \quad (2)$$

with $\eta$ is the dynamic viscosity of the fluid ($=10^{-3}$ Pa s for water), r the radius of the bead and v its speed.

The speed of a bead (in equilibrium) in the x-direction is then given by equation 3:

$$F_M = F_W \Rightarrow v = -\mu_0 \chi \frac{d}{dx}|H^2|\frac{1}{6\pi\eta r} \quad (3)$$

For an average speed of 5 µm/s and a chamber height of 50 µm, it will take 10 s to reach the surface of the sensor, and thus the pre-incubation process will be 10 s. The pre-incubation time can be tuned by changing the height of the chamber, the size of the beads and the strength of the magnetic field.

By way of illustration, the present invention not being limited thereto, an example of detection according to the present invention is provided and different stages of the manufacturing process are discussed Appliance of the Reagent:

Magnetic particles (500 nm COOH Masterbeads (Ademtech) coated with anti-opi antibodies, stored in storage buffer (Ademtech)) were washed three times and were re-suspended in a drying buffer (10 mg/ml BSA, 10% sucrose, 0.1% tritonx405, 10 mM Tris HCl pH 7.1) using a magnetic washing step known to the person skilled in the art. The final magnetic bead concentration was adapted to 1 wt %. A small droplet of this reagent 4 was placed on a carrier surface 3 comprised in the channel 18 of a lid 8 as described on FIG. 2a. The reagent was dried in air for 1 h and stored in a sealed box with silica pouches.

Forming of the Device:

The lid 8 was assembled to a sensor supporting element 10 as described in FIGS. 4a and 4b to form a device 1 as described in FIGS. 5a and 5b. The sensor was of a magnetic type, i.e. a giant magnetic resistance sensor (GMR sensor). The sensor surface was coated with a 1 g/ml solution of BSA-OPI (the OPI-analogue) in coating buffer (10 mM sodium borate, 50 mM NaCl, 0.05% Tween20, pH 9.0). BSA-morphine is the OPI-analogue. A coil suitable for magnetic actuation was provided under and above the device.

Figure 6:
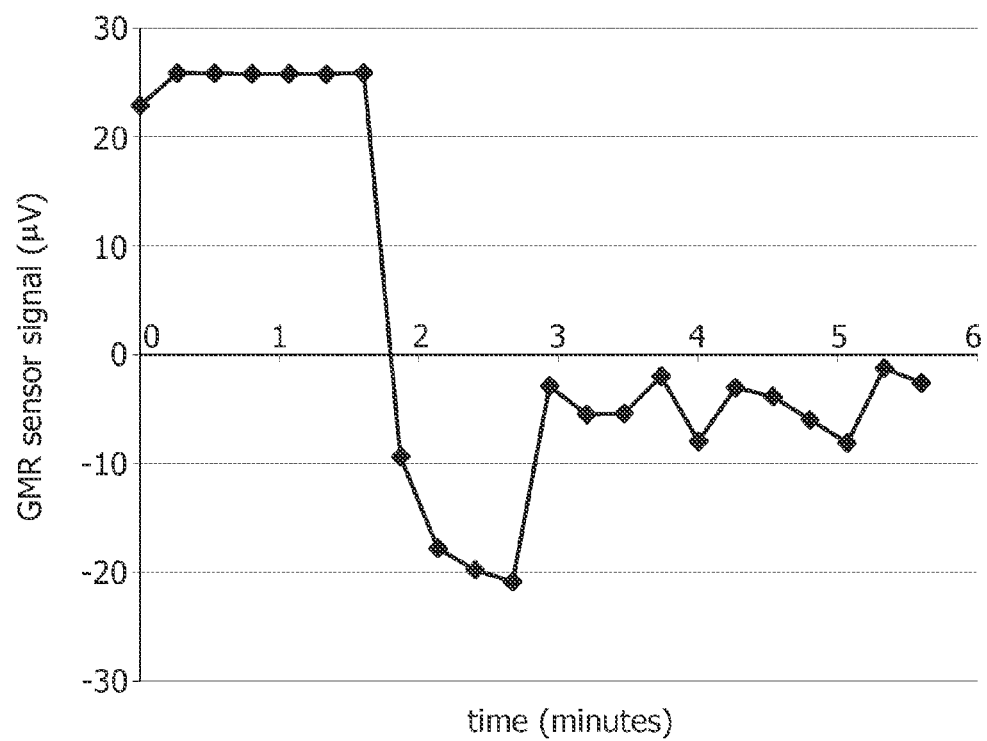
FIG. 6 shows a signal response measured using a sensor device according to an exemplary embodiment of the present invention.

The device 1 was connected to a reader via a flex foil 16, and the magnetic attraction was started by turning on the coil below the device 1. FIG. 6 shows the GMR signal as a function of time. The initial value is roughly 25 µV. A sample fluid composed of a buffer (0.08 M sodium/potassium phosphate, pH 8.1-8.2 containing 0.4 M sodium chloride, 0.05% (w/v) sodium azide and 0.1% (w/v) Triton-X405) (not containing antigens) was injected in the device via an inlet 6 and the reagent was allowed to disperse under magnetic actuation. The magnetic beads, bearing anti-OPI antibodies, now in free suspension in the sample fluid were attracted for 65 seconds toward the sensor surface 5. During this laps of time, the GMR signal dropped, indicating the sensing of the magnetic beads by the sensor. Afterwards, the top coil was turned on and the bottom coil turned off and the unbound and aspecifically bound magnetic beads were repelled from the surface. All unbound beads were removed from the sensor surface and gathered at the top of the chamber, in the vicinity of the carrier surface. The signal representing the binding of the magnetic labels is given by the reduction in GMR signal. The GMR signal reduction is 30.2 V. FIG. 6 shows the GMR sensor signal as a function of time.

This experiment indicates that a reagent 4 applied on a carrier surface 3, in the present example being the roof of the detection chamber 2, i.e. a surface facing the sensor surface 5 and delimiting one side of the detection chamber 2 distinct from the sensor surface 5 can efficiently be liberated and mixed with a sample fluid, and the magnetic labels can be bound to the surface.

By way of illustration, a further example is provided, illustrating features and advantages of embodiments of the present invention. A dose-response curve was measured for a competitive Morphine assay using magnetic particles dried in a fluidics device according to an embodiment of the present invention. In the present example, the invention not being limited thereto, the sensor was prepared as follows:

In order to provide the reagents comprising the magnetic beads, the top part of the fluidics device, e.g. as illustrated by the top part 4 of the fluidic device shown in FIG. 1a, was in the present example first cleaned by soaking the part in Isopropyl alcohol for 5 minutes, and thereafter drying the part in a nitrogen flow. A drying buffer then was prepared containing 10 mM Tris-HCl pH7.5, 10% sucrose, 10 mg/ml BSA and 0.1% tween20. Superparamagnetic particles (Ademtech 500 nm COOH coated particles) were coated with anti-opiate antibodies. The particles were redispersed at 4 wt % in the drying buffer by adding 40 µl buffer to 40 µl immobilised magnetic beads, holding the mixture against a magnet, removing the fluid and redissolving the obtained mixture in 10 µl drying buffer. Subsequently 150 nl of this magnetic bead solution was applied to the top part of the fluidics device. The top part was subsequently stored dry, in a sealed box in the neighbourhood of water absorbing material, such as silica.

The bottom part, e.g. as illustrated by bottom part 5 of the fluidics device, was coated with BSA-Morphine according to the following procedure: The bottom part was first cleaned by providing it in a nitrogen flow. A 10 µg/ml BSA-morphine solution was then prepared by mixing 196 µl of coating buffer with 4 µg/ml of BSA-morphine (100 µg/ml). The coating buffer thereby was made by mixing 15 mM Sodiumcarbonate having a density 1.59 g/l and a molecular weight of 106 g/mol with 35 mM Sodiumbicarbonate having a density of 3.94 g/l and a molecular weight of 84 g/mol and with 0.05% Na-azide having a density of 0.5 g/l, adjusting its pH to 9.6 and storing it at 4° C. A droplet of 2 µl of BSA-morphine solution was applied to the bottom part of the fluidics device, this was incubated in a moist environment O/N at room temperature and thereafter the part was rinsed with cleaning liquid, in the present example being milliQ. The part was further soaked for 30 minutes in a solution of 1×PBS (Phosphate Buffered Saline) and 0.05% Tween20, dried in a nitrogen flow and stored in a sealed box near a water absorbing material such as silica bags.

The top and bottom part of the biosensor was assembled by using tape, and the sensors were kept under dry conditions at room temperature. After 24 hrs the redispersion quality and antibody activity was tested by doing a competitive assay in the optical biosensor system. The assay comprised addition of buffer spiked with Morphine in the fluidic device by autonomous filling through a capillary channel, redispersion of the beads and subsequent attracting the magnetic beads to the sensor surface (with an actuation means, such as e.g. a bottom magnet). The buffer added was a 2× concentrated AJ buffer with $Na_2HPO_4$ 10.76 g/l, $KH_2PO_4$ 0.577 g/l, NaCl23.38 g/l and 0.01% Na-azide which was stored at RT and to which, before use, 0.1% Triton X-405 was added combined with a controlled amount of morphine. Using a plurality of sensors prepared as indicated above, the response to different morphine concentrations was tested by adding different morphine concentrations, i.e. whereby 17 µl AJ buffer, AJ buffer with 1 ng/µl morphine, with 2 ng/µl morphine, with 3 ng/µl morphine, with 4 ng/µl morphine, with 5 ng/µl morphine, with 7.5 ng/µl morphine and with 10 ng/µl was respectively added to different prepared sensor devices. The last step was a magnetic washing step, e.g. using an additional magnet at the top of the device. The total assay time (filling, redispersion and magnetic actuation) was 50 s.

Figure 7:
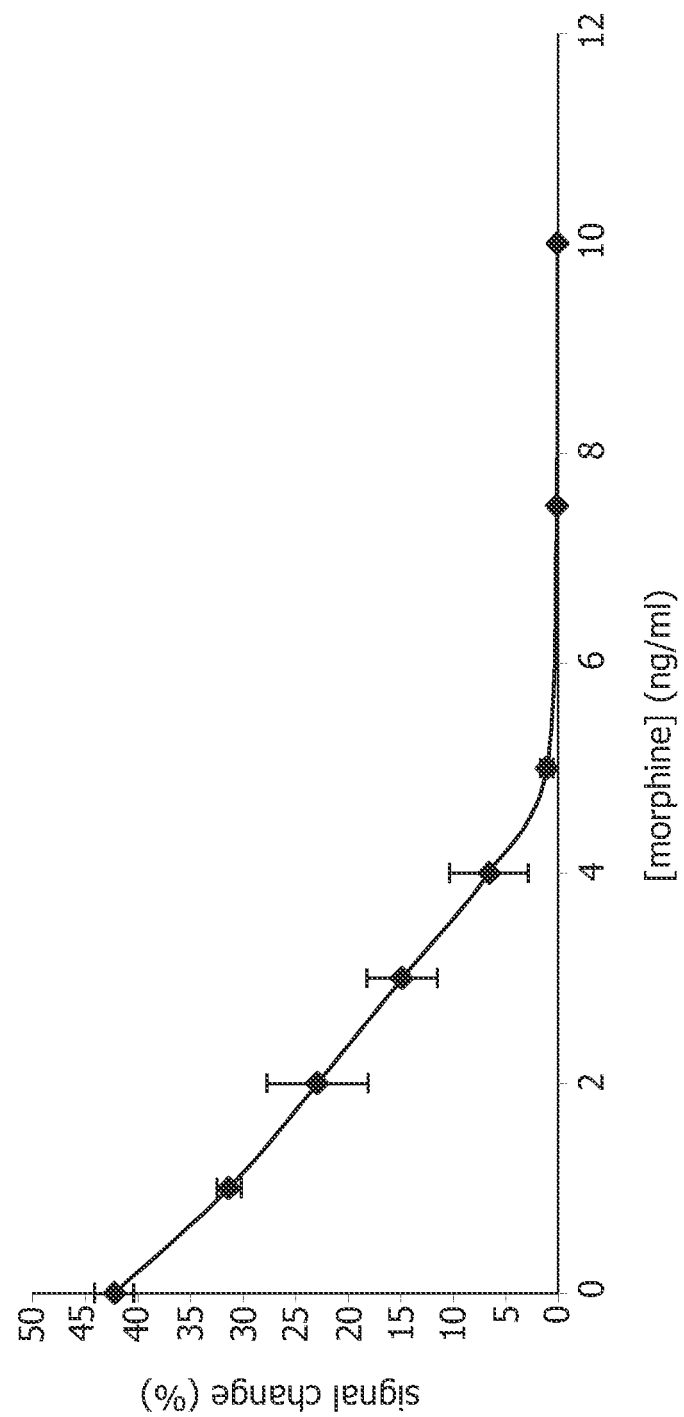
FIG. 7 shows a dose response curve for magnetic beads on a coated surface using a sensor device according to an exemplary embodiment of the present invention.

The dose response curve for the above described assays are shown in FIG. 7 for the different morphine concentrations. The datapoints for morphine concentrations of 5 ng/µl or lower were measured in five-fold, whereas the remaining two datapoints for higher morphine concentrations were measured in duplicate. The graph illustrates the response of the sensor on morphine by indicating the signal change in percentage as function of the amount of morphine added. The above example illustrates one of the large number of possible detection applications for which the sensor can be used.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A device for detecting the presence of an analyte in a sample fluid, the device comprising:
   a detection chamber having a fixed volume, said detection chamber being delimited by two sides and at least partly delimited by distinct carrier and sensor surfaces, the carrier surface and the sensor surface being arranged to face each other and being both accessible to the sample fluid from within the detection chamber,
   the carrier surface comprising a reagent or components thereof deposited only on the carrier surface,
   wherein the reagent or components thereof is/are present in a dissolvable matrix, and the reagent comprises one or more probes which are coupled to magnetic or magnetizable particles,
   the sensor surface being configured to sense the sample fluid within the detection chamber;
   wherein the distance between the carrier surface and the sensor surface is such that the interaction time between the sample fluid and the reagent is in the range from 1 to 60 seconds, and
   wherein said device further comprises:
   at least a magnetic retainer for retaining the reagent or components thereof on the carrier surface; wherein the magnetic retainer comprises at least two magnetic actuators facing one to the other, and positioned on either sides of the detection chamber;
   an inlet for delivering the sample fluid into the device, said inlet for the sample fluid comprising a capillary section with dimensions such that the sample fluid can be driven therein via capillary forces, and said inlet for the sample fluid being remote from the reagent or components thereof;
   an outlet for removing a fluid from the device; and
   a fluidic channel on both sides of the detection chamber, said fluidic channel being connected to said inlet and to said outlet such that the detection chamber presents an enlarged volume towards the inlet and/or the outlet.

2. The device according to claim 1, wherein the volume of the detection chamber is comprised between 0.1 µl and 1 µl.

3. The device according to claim 1, wherein the dimensions of the capillary section of the inlet for the sample fluid are 0.1 to 2 mm.

4. The device according to claim 1, wherein the carrier surface is not co-planar with the sensor surface.

5. The device according to claim 4, wherein a distance between the carrier surface and the sensor surface is tunable.

6. The device according to claim 4, wherein a distance between the carrier surface and the sensor surface is between 30 µm and 500 µm.

7. The device according to claim 1, wherein the detection chamber comprises a sloping wall that slopes towards the sensor surface.

8. The device according to claim 1, wherein the detection chamber has a volume of 0.1 µl to 1 µl.

9. The device according to claim 1, further comprising an actuator, other than the magnetic actuator of the magnetic retainer, for moving the reagent or components thereof in the sample fluid within the detection chamber.

10. The device according to claim 1, wherein the reagent is comprised in a soluble material.

11. The device according to claim 1, wherein the reagent is comprised in one or more lyophilised beads.

12. The device according to claim 1, wherein the carrier surface is non-porous.

13. A process for manufacturing a device for detecting the presence of an analyte in a sample fluid, the process comprising:
    providing a carrier surface,
    depositing a reagent component in a dissolvable matrix only on to the carrier surface,
    providing a sensor surface distinct from the carrier surface,
    forming a detection chamber having a fixed volume, said detection chamber being delimited by two sides and at least partly delimited by the carrier surface and the sensor surface,
    positioning a sensor to sense the sample fluid within the detection chamber, wherein said sensor surface is at a distance from the carrier surface such that the interaction time between the sample fluid and the reagent is in the range from 1 to 60 seconds,
    and wherein said process further comprises the steps of:
    forming an inlet for sample fluid at a location remote from the reagent on said carrier surface for introducing the sample fluid to the reagent within the detection chamber, said inlet for the sample fluid comprising a capillary section with dimensions such that the sample fluid can be driven therein via capillary forces, and
    forming an outlet for passage of a fluid from the detection chamber that is displaced by the sample fluid, wherein the detection chamber is formed to present an enlarged volume to the inlet and/or outlet.

14. The process according to claim 13, the process further comprising an act of drying the reagent on the carrier surface.

15. The process according to claim 13, further comprising an act of freeze-drying the reagent.

16. The process according to claim 13, further comprising an act of providing magnetic actuation means below and/or above the detection chamber.

17. The process according to claim 13, further comprising an act of providing magnetic retention means above the detection chamber.

18. The process according to claim 13, comprising an act of tuning a distance between the carrier surface and the sensor surface.

19. The process according to claim 13, wherein forming the detection chamber comprises an act of assembling the detection chamber using the sensor surface and the carrier surface, after depositing the reagent.

20. The process according to claim 13, wherein the process comprises an act of depositing the reagent on the carrier surface after the detection chamber has been formed.

21. A method for detecting the presence of an analyte in a sample fluid, the method comprising acts of:
provided a device comprising:
a detection chamber having a fixed volume, said detection chamber being delimited by two sides and at least partly delimited by
a carrier surface accessible to the sample fluid from within the detection chamber, the carrier surface comprising a reagent deposited only on the carrier surface in a dissolvable matrix, and
a sensor surface configured to sense the sample fluid within the detection chamber, the sensor surface being distinct from the carrier surface,
an inlet for sample fluid, said inlet for sample fluid comprising a capillary section with dimensions such that the sample fluid can be driven therein via capillary forces, and being remote from the reagent on said carrier surface, and
an outlet for passage of a fluid from the detection chamber that is displaced by the sample fluid,
wherein the detection chamber is provided to present an enlarged volume to the inlet and/or outlet;
introducing the sample fluid into said detection chamber via said inlet for sample fluid,
contacting the sample fluid with the reagent deposited on said carrier surface thereby forming a fluid mixture within the detection chamber, the carrier surface being accessible to the sample fluid while the sample fluid is within the detection chamber,
contacting the fluid mixture with the sensor surface within the detection chamber, the sensor surface being distinct from the carrier surface delimiting the detection chamber and being at a distance from the carrier surface such that the interaction time between the sample fluid and the reagent is in the range from 1 to 60 seconds, and
detecting within the detection chamber through the sensor surface an interaction between the fluid mixture and the sensor surface.

22. The method according to claim 21, wherein the method further comprises an act of magnetically actuating and/or retaining the magnetic or magnetizable particles within the detection chamber before the detecting.

23. The device according to claim 1, wherein the reagent comprises a probe labeled with a magnetic or magnetizable particle.

24. The process of 13, wherein the reagent comprises a probe labeled with a magnetic or magnetizable particle.

25. The method of claim 23, wherein the reagent comprises a probe labeled with a magnetic or magnetizable particle.

26. The device according to claim 2, wherein the dimensions of the capillary section of the inlet for the sample fluid are 0.1 to 2 mm.

27. The device according to claim 1, wherein the distance between the carrier surface and the sensor surface is such that the interaction time between the sample fluid and the reagent is in the range from 5 to 60 seconds.

28. The device according to claim 2, wherein the distance between the carrier surface and the sensor surface is such that the interaction time between the sample fluid and the reagent is in the range from 5 to 60 seconds.

* * * * *